United States Patent
Sbutega et al.

(10) Patent No.: US 12,016,883 B2
(45) Date of Patent: Jun. 25, 2024

(54) PRIMARY T-CELL EXPANSION

(71) Applicant: NantBio, Inc., Culver City, CA (US)

(72) Inventors: Krsto Sbutega, Culver City, CA (US);
Peter Sieling, Culver City, CA (US);
Adam D. Lazar, Culver City, CA (US);
Kayvan Niazi, Culver City, CA (US)

(73) Assignee: NantBio, Inc., Culver City, CA (US)

( * ) Notice: Subject to any disclaimer, the term of this patent is extended or adjusted under 35 U.S.C. 154(b) by 301 days.

(21) Appl. No.: 17/033,265

(22) Filed: Sep. 25, 2020

(65) Prior Publication Data

US 2021/0093669 A1 Apr. 1, 2021

Related U.S. Application Data

(60) Provisional application No. 62/906,319, filed on Sep. 26, 2019.

(51) Int. Cl.
| | |
|---|---|
| *A61K 35/17* | (2015.01) |
| *A61K 45/00* | (2006.01) |
| *C07K 16/28* | (2006.01) |
| *C12N 5/0783* | (2010.01) |

(52) U.S. Cl.
CPC .............. *A61K 35/17* (2013.01); *A61K 45/05* (2013.01); *C07K 16/2806* (2013.01); *C07K 16/2809* (2013.01); *C07K 16/2818* (2013.01); *C12N 5/0636* (2013.01); *C12N 2501/20* (2013.01)

(58) Field of Classification Search
None
See application file for complete search history.

(56) References Cited

U.S. PATENT DOCUMENTS

| | | | |
|---|---|---|---|
| 7,977,095 | B2 | 7/2011 | Bonyhadi et al. |
| 9,220,731 | B2 | 12/2015 | Berry et al. |
| 2004/0001829 | A1 | 1/2004 | June et al. |
| 2010/0135998 | A1* | 6/2010 | Bowman .............. A61K 39/395 435/375 |
| 2013/0034898 | A1 | 2/2013 | Berry et al. |
| 2013/0058909 | A1 | 3/2013 | Szabolcs |
| 2015/0065359 | A1 | 3/2015 | Rustgi |
| 2016/0083682 | A1 | 3/2016 | Berry et al. |
| 2016/0108358 | A1 | 4/2016 | Curcio |
| 2017/0037370 | A1 | 2/2017 | Kaiser et al. |
| 2019/0062735 | A1* | 2/2019 | Welstead ................. C12N 9/22 |
| 2019/0345536 | A1* | 11/2019 | Sasaki .................. C12N 5/0636 |
| 2020/0325494 | A1* | 10/2020 | Rawlings ................. C12N 9/22 |
| 2022/0175836 | A1* | 6/2022 | Lum .............. A61K 39/001106 |
| 2022/0228115 | A1* | 7/2022 | Hux .................... C12N 15/1138 |
| 2022/0282285 | A1* | 9/2022 | Webber .................. C12N 15/11 |

FOREIGN PATENT DOCUMENTS

| | | |
|---|---|---|
| EP | 4034641 A1 | 8/2022 |
| WO | 03/024989 A2 | 3/2003 |
| WO | 2006/124412 A2 | 11/2006 |
| WO | 2015/164745 A1 | 10/2015 |
| WO | 2019067951 A3 | 7/2019 |
| WO | 2021062267 A1 | 4/2021 |

OTHER PUBLICATIONS

International Preliminary Report on Patentability received for PCT Application Serial No. PCT/US2020/052874 dated Apr. 7, 2022, 7 pages.
Wherry E John, "T cell exhaustion", Nature Immunology, Jun. 2011, vol. 12, No. 6, pp. 492-499 (Cited from Specification).
Zhou et al., "Telomere length of transferred lymphocytes correlates with in vivo persistence and tumor regression in melanoma patients receiving cell transfer therapy", The Journal of Immunology, 2005, vol. 175, pp. 7046-7052 (Cited from Specification).
Sagerström et al., "Activation and differentiation requirements of primary T cells in vitro", Proc. Natl. Acad. Sci., 1993, vol. 90, pp. 8987-8991.
International Search Report and Written Opinion received for PCT Application Serial No. PCT/US2020/052874 dated Jan. 13, 2021, 13 pages.
Extended European Search Report received for EP Application Serial No. 20869508.0 dated Dec. 4, 2023, 17 pages.
Priesner et al, "Automated Enrichment, Transduction, and Expansion of Clinical-Scale CD62L + T Cells for Manufacturing of Gene Therapy Medicinal Products", Human Gene Therapy, vol. 27, No. 10, Oct. 1, 2016 (Oct. 1, 2016), pp. 860-869.
Partial Supplementary European Search Report received for EP Application Serial No. 20869508.0 dated Aug. 25, 2023, 13 pages.
Kagoya et al., "Transient stimulation expands superior antitumor T cells for adoptive therapy", JCI Insight, Jan. 26, 2017, vol. 2, No. 2, 14 pages.

* cited by examiner

*Primary Examiner* — Michail A Belyavskyi
(74) *Attorney, Agent, or Firm* — Martin Fessenmaier; Umberg Zipser LLP (57) ABSTRACT

Provided herein are methods of in-vitro primary T cell growth that enrich T cells in a blood sample, stimulate the T cells with anti-CD2, anti-CD3, and/or anti-CD28 and that expand the T cells with a cytokine. Also provided are methods of treating a tumor in a patient using the expanded T cells.

9 Claims, 8 Drawing Sheets

PRIMARY T-CELL EXPANSION

This application claims priority to our US Provisional Application with the Ser. No. 62/906,319, which was filed Sep. 26, 2019, and which is incorporated by reference herein.

FIELD OF THE INVENTION

The field of the invention relates to immunotherapy, and specifically to methods of expanding primary T-cells, and using the same.

BACKGROUND OF THE INVENTION

The background description includes information that may be useful in understanding the present invention. It is not an admission that any of the information provided herein is prior art or relevant to the presently claimed invention, or that any publication specifically or implicitly referenced is prior art.

All publications and patent applications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

T cells are the key mediators in cell-mediated immunity. Highly specialized to defend against bacterial and viral infections, T cells also mediate immune surveillance against tumor cells and react to foreign tissues. Given this important function of T cells in the body's defense mechanism, scientists have developed methods for expanding T cells in vitro.

T cell therapy is a rapidly progressing field and optimized protocols for the scalable manufacture of T cells are essential to maximize the therapeutic potential of patient-derived T cells. One such T-cell therapy is disclosed by the applicant in WO/2019/067951 (the '951 disclosure), which is incorporated by reference in its entirety including the drawings. The '951 disclosure provides compositions, methods and uses of genetically modified NKT cells to induce an NKT cell immune response against tumor or to change a microenvironment of the tumor by suppressing an activity of myeloid-derived suppressor cells.

A single administration of adoptive T cell therapy can require billions of expanded T cells. Production of human T cells for cellular therapy is a complex process. While many techniques have been disclosed in the literature on how to expand T cells and optimization for maximum yield, it is also known that long-term expanded T-cells tend to be exhausted, and have reduced efficacy in defending against infections, tumor cells, or foreign tissues.

T-cell exhaustion is characterized by the stepwise and progressive loss of T-cell functions and can culminate in the physical deletion of the responding cells. T-cell exhaustion is often seen in expanded T cells, although the reasons for exhaustion are not clear. Wherry, *Nat Immunol.* (2011) reported that strong TCR stimulation during expansion leads to exhaustion of T cells. Zhou et al, J Immunol. (2005) reported that telomere length may be correlated with efficacy in vivo.

Despite these advancements, it is largely unexplored and unknown how to expand T cells that are not exhausted after the stimulation and expansion steps. Furthermore, while the current methods requires several dilution steps, there remains a need in the art for new methods that allows expansion of T cells in a continuous fashion, while also following the principles of good manufacturing practice.

SUMMARY OF THE INVENTION

The inventors have developed a new method of expanding primary T cells in which the expanded T-cells do not display the characteristics of exhausted cells. Moreover, the cytotoxic efficacy of such expanded primary T cells is comparable to the control (native) T cells. Furthermore, the methods disclosed herein allow for a continuous culture method wherein the cells can grow continuously without encountering irregularities from high density of cells or from multiple dilution steps.

In one aspect of the inventive subject matter, the inventors contemplate a method of in-vitro primary T cell growth, comprising: enriching T cells in a blood sample; stimulating the T cells with anti-CD2, anti-CD3, and/or anti-CD28; expanding the T cells with a cytokine; and harvesting the expanded T cells. Preferably, the cytokine is IL-2, IL-7, and/or IL-15. The blood sample may comprise peripheral blood mononuclear cells (PMBC). The step of expanding the T cells with a cytokine may comprise serial dilution of the T cells and the cytokine in cell culture medium. Furthermore, the cell culture medium is optimized to culture human T-cells. The cell culture medium may further comprise human serum, typically about 10% of the total volume of the cell culture medium.

Preferably, the methods disclosed herein are performed in a Good Manufacturing Practice (GMP) in-a-box system. The expanded T cells may be frozen for further use, or may be used immediately by phenotyping or transfecting the expanded T cells.

In one aspect of the inventive subject matter, the inventors contemplate a method treating a tumor in a patient, comprising: receiving a blood sample from the patient; expanding T cells in the blood sample by isolating T cells from the blood sample, stimulating the T cells, expanding the stimulated T cells, and harvesting the T cells; transfecting the expanded T cells with a recombinant polynucleotide construct; and treating the disease by reintroducing the transfected cells to the patient. The transfection may be done by a viral particle, or by electro-transfection. The tumor may be a cancer, wherein the cancer is selected from the group consisting of: melanoma, squamous cell carcinoma, breast cancer, head and neck carcinoma, thyroid carcinoma, soft tissue sarcoma, bone sarcoma, testicular cancer, prostatic cancer, ovarian cancer, bladder cancer, skin cancer, brain cancer, angiosarcoma, hemangiosarcoma, mast cell tumor, primary hepatic cancer, lung cancer, pancreatic cancer, gastrointestinal cancer, renal cell carcinoma, and hematopoietic neoplasia.

Various objects, features, aspects and advantages of the inventive subject matter will become more apparent from the following detailed description of preferred embodiments.

DETAILED DESCRIPTION

The inventors have now developed a novel method of expanding primary T cells. The method comprises the steps of: (a) enriching T cells in a blood sample; (b) stimulating the T cells with anti-CD2, anti-CD3, and/or anti-CD28; (c) expanding the T cells with a cytokine; and (d) harvesting the expanded T cells.

The initial step for enriching T cells in a blood sample is contemplated to include the isolation of peripheral blood mononuclear cells (PBMCs). This can typically and efficiently be achieved with the help of a solution that forms a density gradient to trap PMBCs in a specific layer, which is typically done with the help of a centrifuge. Isolation of the T cells may also be done by using a commercially available T cell isolation kit, such as those sold by Biolegend, MojoSort™ Human CD8 T Cell Isolation Kit.

The so isolated T cells are then stimulated with an anti-CD2 antibody, an anti-CD3 antibody, and/or an anti-CD28 antibody. The stimulation phase is considered to be the first step that occurs before division, which commits the cell to enter the cell cycle, requiring a number of signals to promote progression through the cell cycle. Activated T cells include but are not limited to one or more selected from the group consisting of cytotoxic T cells, assisted T cells, natural killer T cells, gamma delta T cells, regulatory T cells, and memory T cells. In the stimulation step, the T cells may be incubated with anti-CD2, anti-CD3, and/or anti-CD28 antibodies (all of which are commercially available) for at least 1 hr, 2 hrs, 3 hrs, 4 hrs, 6 hrs, 12 hrs, 18 hrs, 24 hrs, or up to 2 days. The cell culture medium is typically one that is specifically designed for culturing T cells. Alternatively, it may be a medium that is commercially available for culturing cells, such as for example, RPMI 1640 Medium available from Thermo Fisher Scientific.

The so stimulated T cells are then cultured in a culture medium containing IL-2, IL-7, and/or IL-15 cytokines. Differentiation and expansion, leading to changes which effect the future functional and survival potential of the progeny cells, also occurs during this step. The differentiation of naive CD4 T cells into polarized effectors in vitro is dependent on the interaction of multiple co-stimulation receptor/coreceptor pairs, growth-promoting cytokines, like IL-2, and polarizing cytokines. IL-12 or IFN-g, and the lack of IL-4, generate Th1-polarized effectors (capable of IL-2, IFN-g, TNF-α, and TGF-b production), whereas the presence of IL-4 and the lack of IFN-g generate Th2-polarized effectors (capable of IL-4, IL-5, IL-10, and IL-13 production). Thus, the presence of these cytokines are advantageous for various reasons—to illustrate, cytokines such as IL-2 and IL-7 help to convert T cells into memory cells. The cell culture may be for at least 1 day, 2 days, 3 days, 4 days, 5 days, 6 days, 7 days, 8 days, 9 days, or 10 days.

The step of expansion typically comprises serial dilution of the T cells and cytokine in cell culture medium. The cell culture medium is typically optimized to culture human T cells, such as enriched RPMI+human serum (10%). Serial dilution preferably means increase of the total culture volume by 2-, 4-, 8-, 16- or 32-fold every 3-, 4-, 5-, 6-, or 7-days. Notably, the inventors found that this type of serial dilution and culture volume increases resulted in cell expansion and cell viability without any significant effects on the activation phenotype of expanded cells.

The serial dilution is preferably done in a continuous culture device, such as the one disclosed in US20130034898A1, which is incorporated by reference herein in its entirety. In one embodiment, the serial dilution comprises having an inlet and exit of cell culture medium to permit an adequate flow to each growth surfaces. The cell culture fluid distribution may be analyzed using computational fluid dynamics and key metabolite utilization analysis to assure that the T cells are not subject to detrimental growth conditions. Thus, while serial dilution of the T cells is contemplated during the expansion step, such serial dilution may be performed in a single device.

Furthermore, the T-cells are preferably expanded in a system that ensures that the products are consistently produced and controlled according to quality standards. It is designed to minimize the risks involved in any pharmaceutical production. In other words, the method disclosed herein contemplates that the T cells are expanded by following the protocols of a good manufacturing practice (GMP). In one embodiment, the method for expanding primary T cells may be performed, for example, in a GMP in-a-box system. A culture system that functions as a "GMP in-a-box" system can be utilized using the Austrianova's Cleanroom setup, or using a device as described by US20150065359, or using the culture systems taught by US20160108358 and US20160083682, or using a continuous culturing device as described by U.S. Pat. No. 9,220,731. Each of these references are incorporated by reference herein in its entirety.

The so expanded T cells may be used immediately, for example, for the treatment of a disease as discussed further below, or may be cyropreserved and can later be thawed for further experimentation without compromising their characteristics. This not only enables flexibility with respect to the setup for T cell expansion but also allows spontaneous explorations or verification experiments. The optimal concentration to be used when freezing cells depends on the specific details of the experimental assay. In one embodiment, using a concentration of 10-15 million cells per milliliter may be practical in terms of the logistics of the freezing and thawing processes, for example, the amount of freezing media to be used when freezing the cells and the number of vials to be handled while freezing or thawing.

In another aspect of this disclosure, the inventors have provided methods for treating a disease in a patient. The method comprises receiving blood sample from the patient, and expanding the T cells in the blood as discussed herein. The expanded T cells are then transfected with a polynucleotide construct. The expanded and transfected T cells are then injected to the patient for treating the disease. The disease is usually treated by inducing, maintaining, or augmenting a T-cell response.

In one preferred embodiment, the disease contemplated to be treated with the expanded T-cells is tumor. As used herein, the term "tumor" refers to, and is interchangeably used with one or more cancer cells, cancer tissues, malignant tumor cells, or malignant tumor tissue, that can be placed or found in one or more anatomical locations in a human body.

As used herein, the term "maintaining or augmenting a T cell response" means increasing the number of activated cells expressing a T cell receptor present to provide a cellular immune response to a tumor or cancer cell expressing a particular tumor or cancer neoepitope, antigen or self-lipid. As used herein, the term "immunocompetent cells" includes all cells of the immune system including all lymphocytes, and including but not limited to T cells, B cells, dendritic cells, macrophages, NKT cells and the like.

With respect to the T cells used in the expansion, it is generally contemplated that the T cells may be an autologous T cell from a patient who is seeking treatment for a disease such as cancer. Such autologous T cells may be isolated from whole blood, cord blood, or cultivated from precursor or stem cells using methods well known in the art. Moreover, it should also be appreciated that the T cells need not be autologous, but may be allogenic, or heterologous T cells.

In one embodiment, the T cells can be isolated from other cells in the patient's bodily fluid using flow cytometry (e.g., fluorescence activated cell sorting (FACS), etc.) or magnetic activated cell sorting (MACS). For example, T cells can be isolated from other cells using fluorescence tagged or magnetic-particle tagged antibody. The inventors also contemplate that the isolated cells by flow cytometry or MACS can be further enriched using a pull-down assay with beads coated with peptide antigen. Systems, compositions, and methods of isolating or enriching T cells are known in the art and all of such systems, compositions, and methods are deemed suitable for use herein.

Additionally, the population of isolated and enriched T cells can be further increased via ex vivo expansion of the T cells. The ex vivo expansion of T cells can be performed in any suitable method with any suitable materials that can expand T cells at least 10 times, preferably at least 100 times in 7-21 days. For example, isolated and enriched T cells can be placed in a cell culture media (e.g., AIMV® medium, RPMI1640® etc.) that includes one or more conditions that may include addition of any molecules that can stimulate T cell growth, induce cell division of T, and/or stimulate cytokine release from T cells that can further expand T cells. Thus the activating molecules include one or more cytokines (e.g., IL-2, IL-5, IL-7, IL-8, IL-12, IL-12, IL-15, IL-18, and IL-21, preferably human recombinant IL-2, IL-5, IL-7, IL-8, IL-12, IL-12, IL-15, IL-18, and IL-21, etc.) in any desirable concentration (e.g., at least 10 U/ml, at least 50 U/ml, at least 100 U/ml), T cell receptor antibodies on the surface of genetically modified T cells (e.g., anti-CD2, anti-CD3, anti-CD28, α-TCR-Va24+ antibodies, preferably immobilized on beads, etc.), a glycolipid (e.g., α-GlcCer, β-ManCer, GD3, etc.), a glycolipid coupled with CD1 (e.g., CD1d, etc.), etc.

With respect to these activating conditions, it is contemplated that the dose and schedule of providing activating conditions may vary depending on the initial number of T cells and the condition of the T cells. In some embodiments, a single dose of cytokine (e.g., 100 U/ml) can be employed for at least 3 days, at least 5 days, at least 7 days, at least 14 days, at least 21 days. In other embodiments, the dose of cytokine may be increased or decreased during the expansion period (e.g., 200 U/ml for first 3 days and 100 U/ml for next 14 days, or 100 U/ml for first 3 days and 200 U/ml for next 14 days, etc.). Also it is contemplated that different types of cytokines can be used in combination or separately during the ex vivo expansion (e.g., IL-15 for first 3 days and IL-18 for next 3 days, or combination of IL-15 and IL-18 for 14 days, etc.).

Optionally, the expanded T cells can be further activated under conditions that will increase cytotoxicity. The condition to increases cytotoxicity include contacting the expanded T cells with one or more specific antibodies (e.g., anti-CD2, anti-CD3, anti-CD28, α-TCR-Va24+ antibodies, preferably immobilized on beads, etc.), a glycolipid (e.g., α-GlcCer, β-ManCer, GD3, etc.), or a glycolipid coupled with CD1 (e.g., CD1d, etc.), for a desired period (e.g., at least 1 hour, at least 6 hours, at least 24 hours, at least 3 days, at least 7 days, etc.). The cytotoxicity of the expanded and activated T cells can be determined by measuring the amount of cytokine release (e.g., IL-2, IL-13, IL-17, IL-21, TNF-α, etc.) from the T cells.

Figure 1:
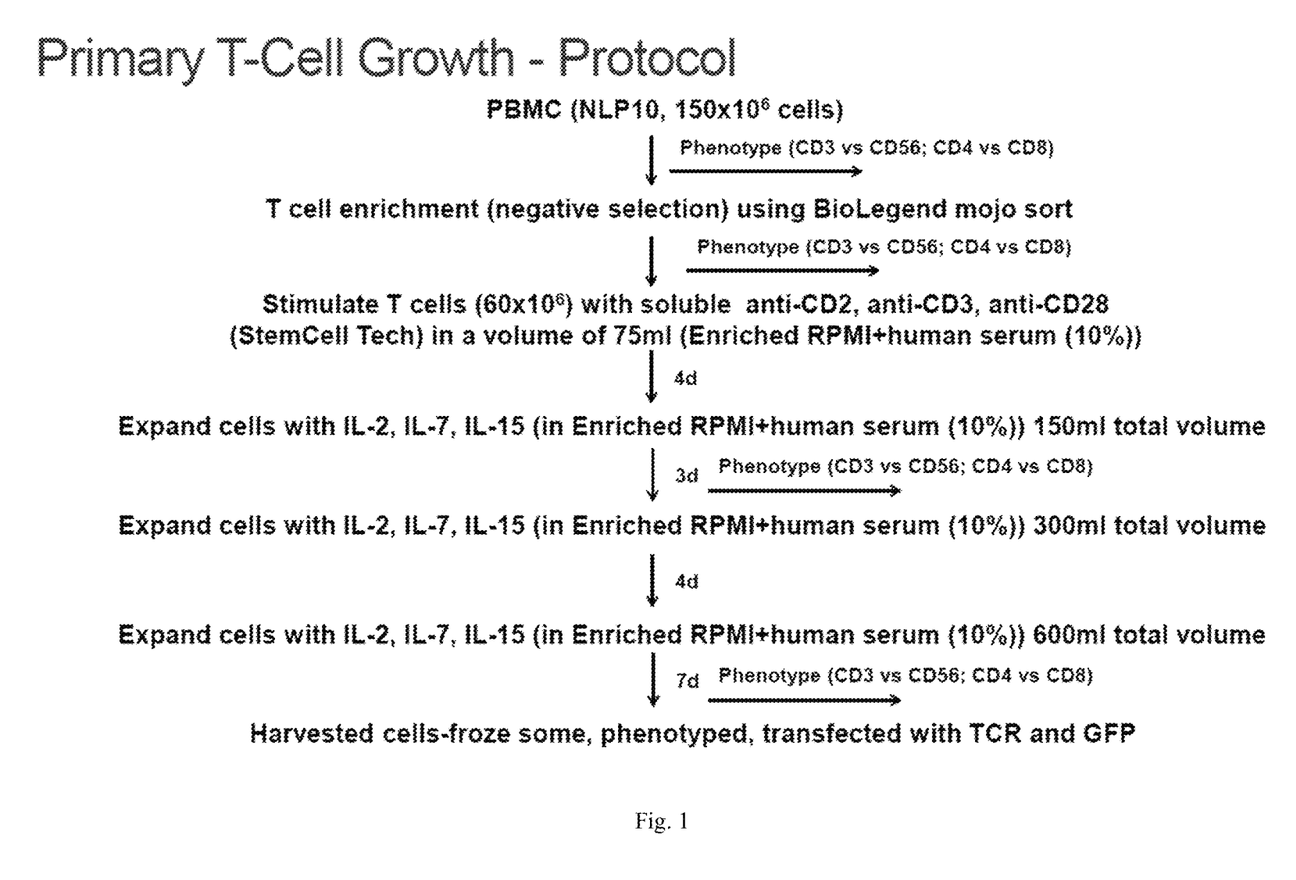
FIG. 1 illustrates a flowchart diagram of the primary T cell growth protocol of the present disclosure.
Figure 2:
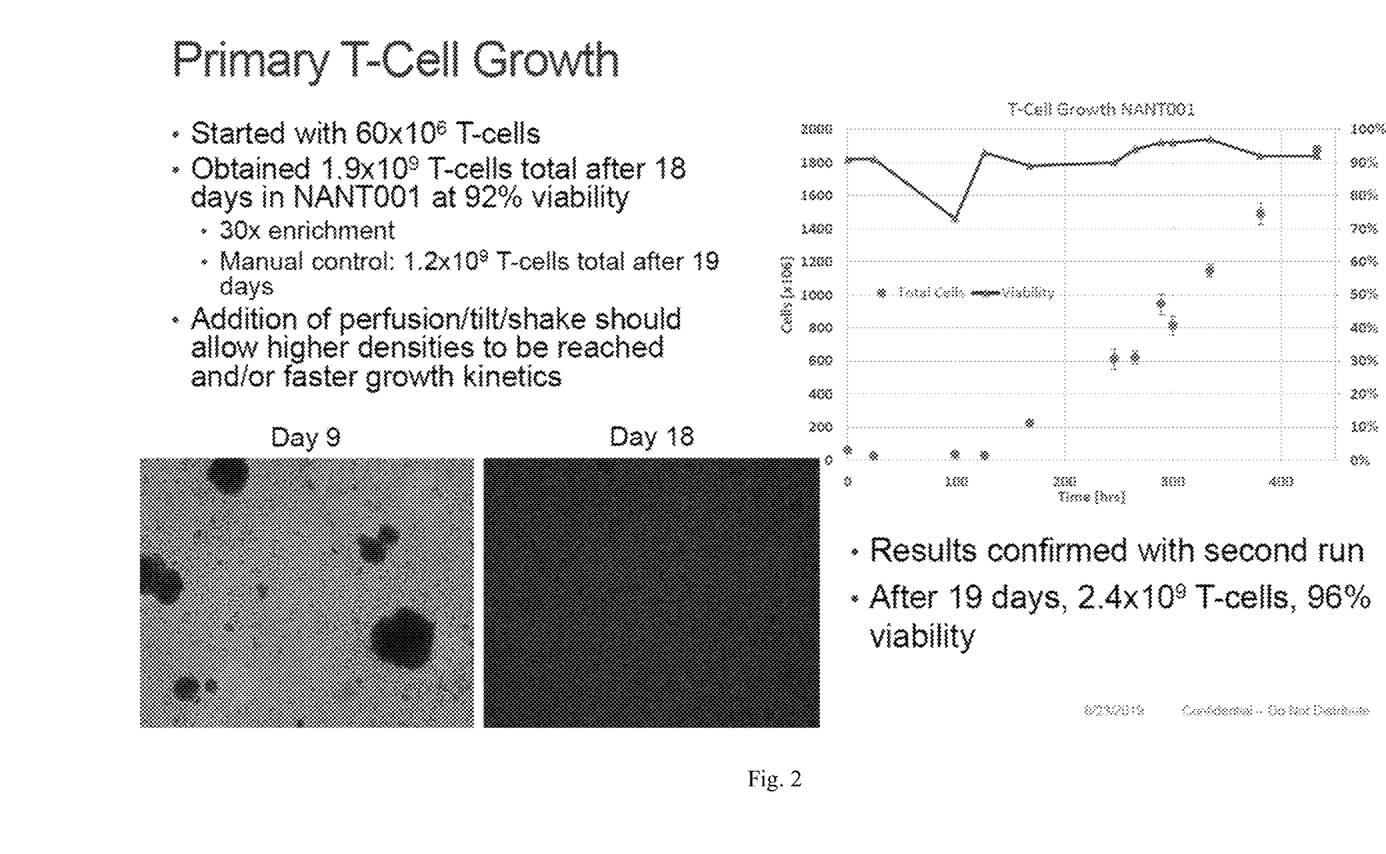
FIG. 2 illustrates a growth chart for primary T cells growth.

A flowchart diagram of an exemplary primary T cell growth protocol as described herein is illustrated in FIG. 1. In one embodiment, as illustrated in FIG. 2, the inventors started with $60 \times 10^6$ T-cells and were able to obtain $1.9 \times 10^9$ T-cells total after 18 days at 92% viability. Thus, the inventors achieved a 30× (30-fold) enrichment. The control experiment resulted in $1.2 \times 10^9$ T-cells total after 19 days. It is contemplated that the addition of perfusion/tilt/shake would allow higher densities to be reached and/or faster growth kinetics. These results were confirmed with second run; in this second run, after 19 days, $2.4 \times 10^9$ T-cells were obtained with 96% viability. The following exemplary procedures describe a typical T cell expansion in GMP-in-a-box-Overall as depicted in FIG. 1.

Isolation of PBMC and enrichment for T cells: Peripheral blood mononuclear cells were isolated using density gradient centrifugation on Ficoll-Paque (Cytiva Cat #17-1440-03). PBMC were frozen in liquid nitrogen for later use.

Figure 3:
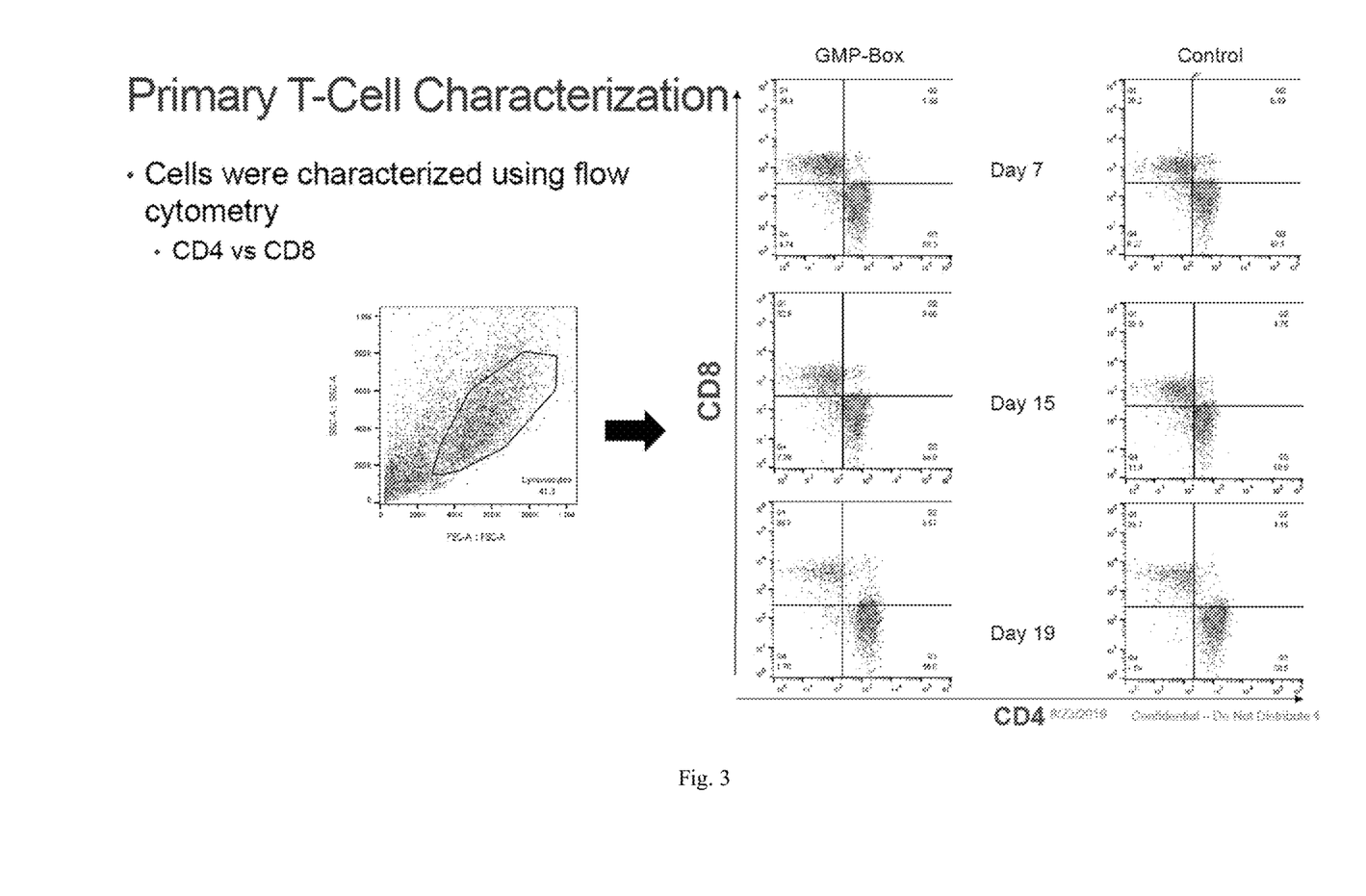
FIG. 3 illustrates one embodiment of expanded primary T cell characterization.
Figure 4:
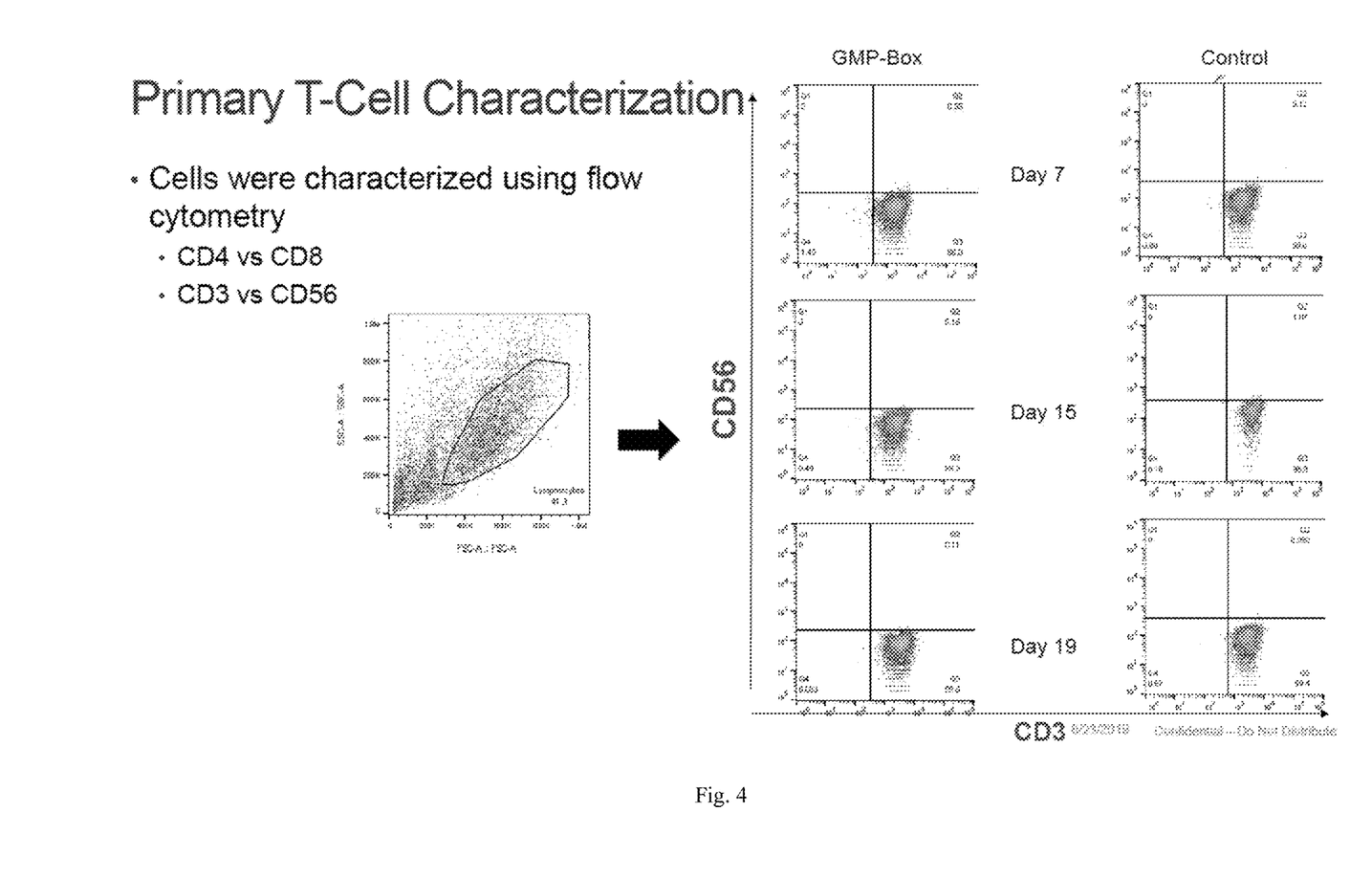
FIG. 4 illustrates another embodiment of expanded primary T cell characterization.
Figure 5:
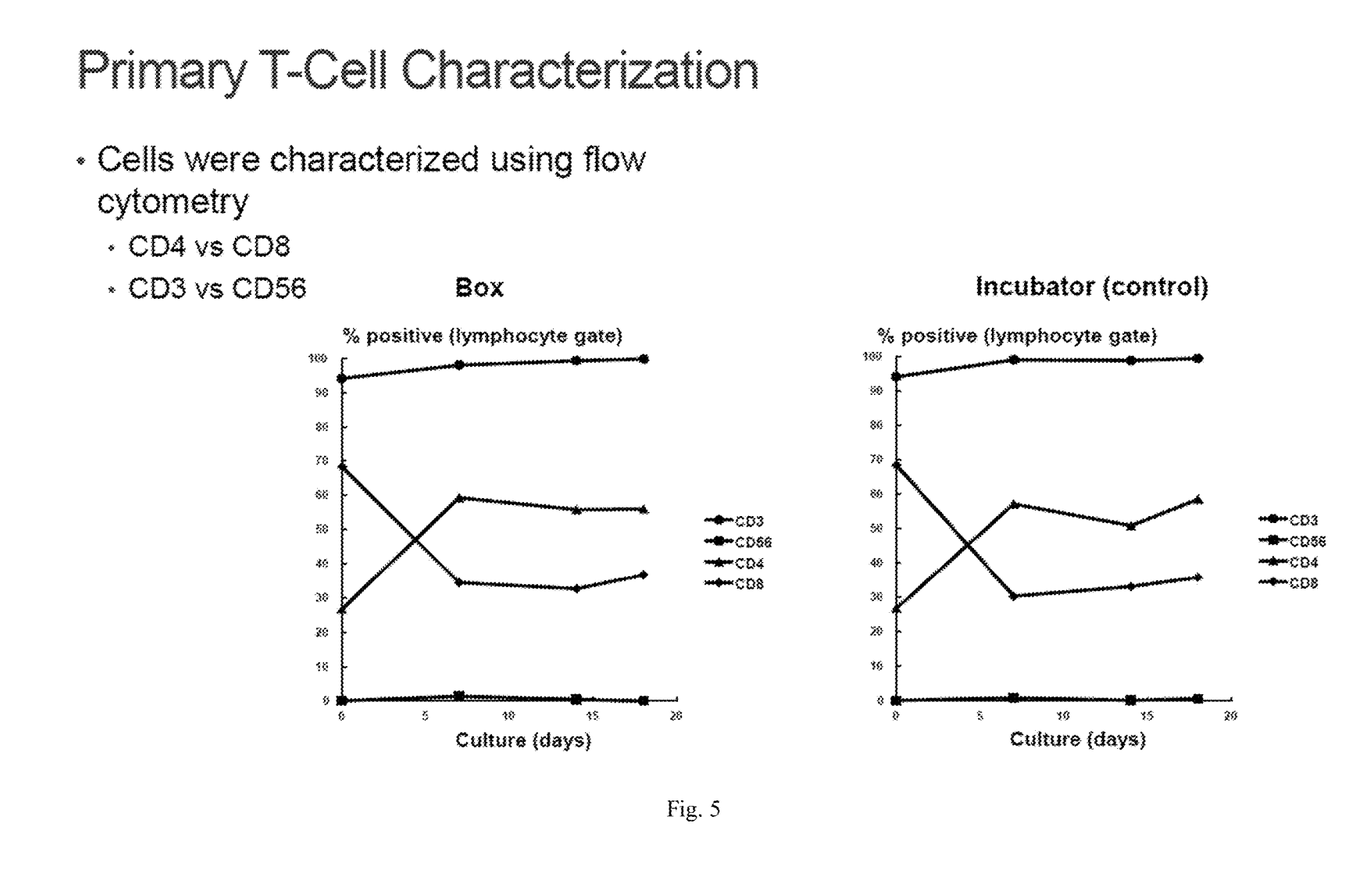
FIG. 5 illustrates another embodiment of expanded primary T cell characterization.

A portion of the PBMC were used to identify the frequency of T cell subpopulations (CD4 and CD8) prior to expansion in the GMP-in-a-box. Briefly, cells were labeled with monoclonal antibodies to human CD4 (BD Biosciences cat #555347) and CD8 (Thermo-Fisher cat #17-0088-42) in addition to CD3 (BD Biosciences cat #555339) as a total T cell population. Since NK cells respond to the growth factors used in our culture system, we also examined NK cell frequency using antibodies to CD56 (Thermo-Fisher cat #MA1-19638). Cells were acquired on a flow cytometer (Thermo-Fisher Attune NxT) and data analyzed using FloJo software. Data are shown in FIGS. 3 and 4 and in summary form for the time course in FIG. 5. T cells were enriched using MojoSort CD3 selection for T cells (BioLegend, cat #480022) using the manufacturer's instructions.

Stimulation of T cells: T cells ($60 \times 10^6$ in 75 ml of Enriched RPMI containing 10% human AB serum Omega Scientific cat #HS-20) with soluble anti-CD3, CD28, CD2 monoclonal antibodies (ImmunoCult Stem Cell Technologies cat #10970). Cells were cultured at 37° C. in a CO2 atmosphere (5%).

Expansion of T cells: Cells were cultured as above for four days. After four days, fresh media was added to the GMP-in-a-box (Enriched RPMI containing 10% human AB serum) enriched with T cell growth factors (human recombinant IL-2 (50 Units/ml) cat #200-02, IL-7 (5 ng/ml) cat #200-07, and IL-15 (50 ng/ml) cat #200-15, all from PeproTech). Media was changed again every 3-4 days for a total of 18-19 days, with a small portion of the cells removed at each feeding in order to evaluate the phenotype of T cell subpopulations. T cell numbers and viability were determined at the same time as phenotype (FIG. 2).

Figure 6:
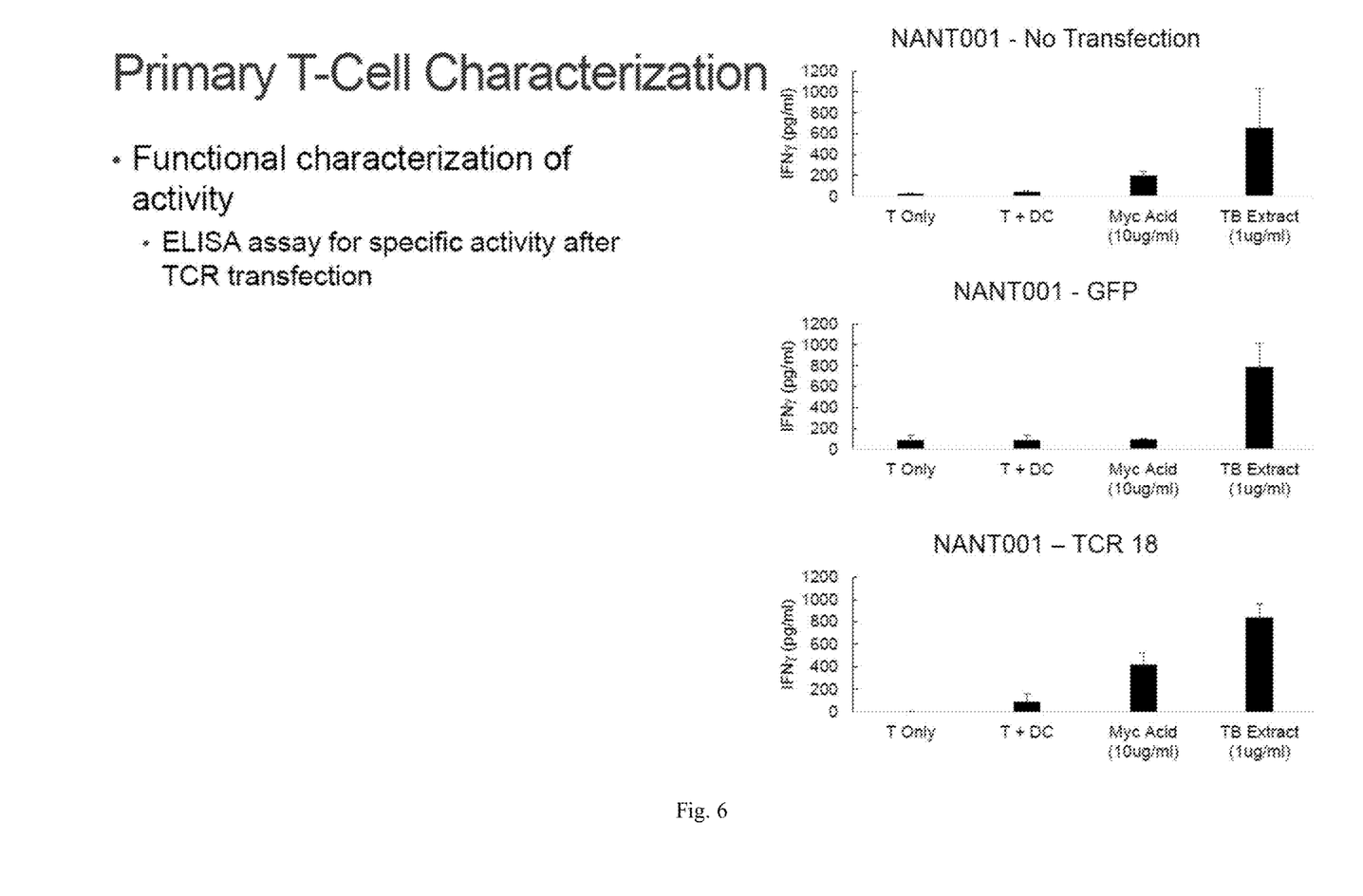
FIG. 6 illustrates the functional characterization of activity of expanded primary T cells as measured by ELISA assay.
Figure 7:
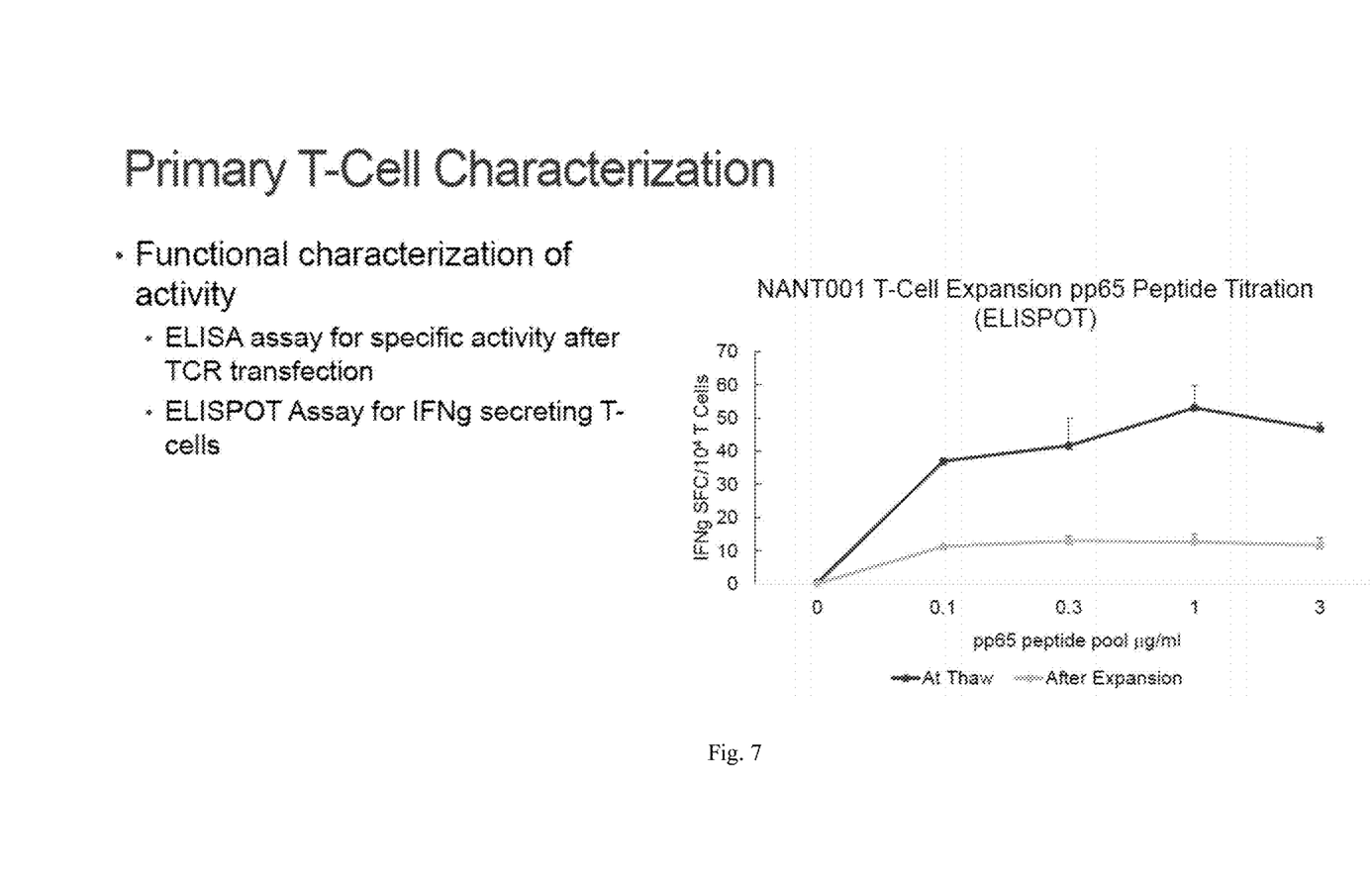
FIG. 7 illustrates another embodiment of functional characterization of activity of expanded primary T cells as measured by ELISPOT assay.

Harvest and examination of function of expanded T cells: On the final day of culture (18-19d), the cells were removed from the GMP-in-a-box, and while some cells were frozen, the function of the T cells was examined by taking the remaining cells (10×10⁶) to transfect with RNA encoding a T cell receptor (TCR) specific for a lipid antigen. The transfected T cells were cultured with appropriate antigen presenting cells pulsed with antigen and IFN-γ production from the T cells evaluated by ELISA (FIG. 6). Alternatively, T cells from a subject with demonstrated reactivity to CMV pp65 protein were expanded then evaluated for reactivity to pp65 (FIG. 7). The T cell response was determined using ELISPOT.

Enriched RPMI recipe: RPMI-1640 with L-glutamine (GIBCO-Invitrogen catalog number 11875-093), to which was added: 5 ml Na-Pyruvate (GIBCO-Invitrogen catalog number 11360-070); 5 ml Pen-Strep L-gln (GIBCO-Invitrogen catalog number 10378-016); 55 µM 2-mercaptoethanol (GIBCO-Invitrogen catalog number 21985-023, 1000×); 10 mM HEPES (GIBCO-Invitrogen catalog number 15630-080, 1M); 2.5 ml Nonessential amino acids (GIBCO-Invitrogen catalog number 11140-050, 100×, 10 mM); 2.5 ml Essential amino acids (GIBCO-Invitrogen catalog number 11130-051, 50×MEM amino acid soln); 10 µg/ml Gentamicin (GIBCO-Invitrogen catalog number 15710-064, 1000×, 10 mg/ml). The so prepared medium was mixed, filtered through 0.2 µm filter unit and stored at 4° C.

The primary T cell characterization is illustrated in FIGS. 3-8. FIG. 3 illustrates characterization of the GMP-box cells (expanded T cells using the instant method) compared to control T cells. CD4 versus CD8 characterization shows that the GMP-box and control look the same, so the presently disclosed method of T-cell expansion leads to similar activity as the control T cells. Furthermore, as illustrated in FIG. 4, CD3 versus CD56 experiments using flow cytometry also shows the similar results with respect to activity. The results of FIG. 3 and FIG. 4 are also shown in a chart format in FIG. 5.

FIG. 6 illustrates the functional characterization of activity as measured by IFNγ. The activity of the expanded T cell (called NANT001) was measured with an ELISA assay without transfection, transfections with a recombinant DNA (GFP) and transfection with a T-cell receptor specific to mycolic acid (TCR18). Notably, these experiments illustrate that the activity of the expanded T cells remain intact after transfection.

FIG. 7 illustrates another example of functional characterization of activity. ELISA assay for specific activity was done after TCR transfection. ELISPOT assay for IFNγ secreting T cells were also done. The results shown here compare expanded T cells after expansion and after a freeze-thaw cycle. Unexpectedly, it can be seen that the expanded T cells have better activity after the freeze-thaw cycle.

Figure 8:
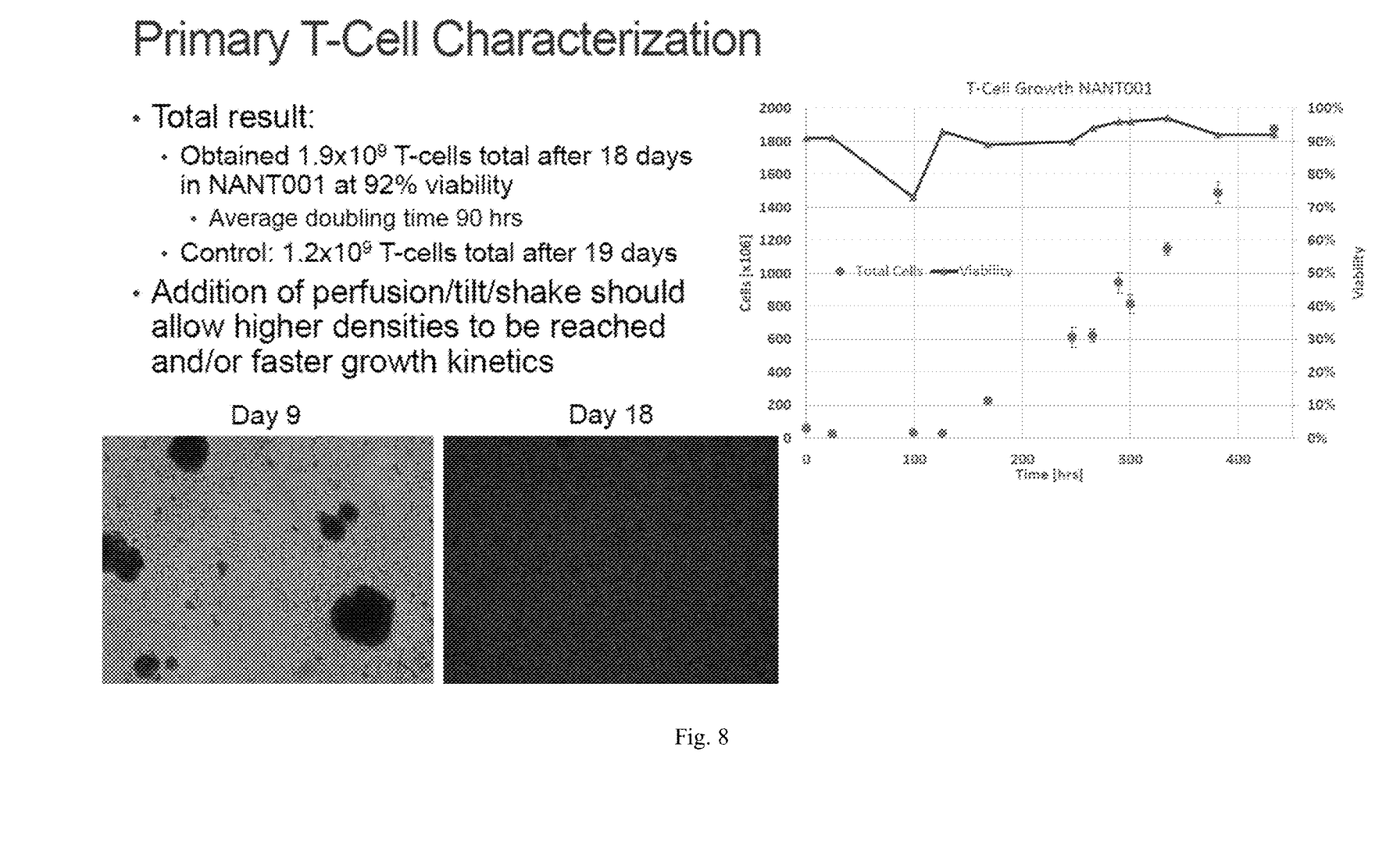
FIG. 8 further illustrates primary T cell characterization.

FIG. 8 further illustrates primary T cell characterization. The results in FIG. 8 shows that 1.9×10⁹ T-cells were obtained after 18 days in NANT001 at 92% viability. The average doubling time was 90 hours. The control yielded 1.2×10⁹ T-cells total after 19 days. The inventors contemplate that addition of perfusion/tilt/shake should allow higher densities to be reached and/or faster growth kinetics.
Treatment of Tumor.

The expanded T cells may be used to treat a disease such as tumor by transfecting the T cells with a recombinant polynucleotide, and reintroducing or administering the transfected cells back to the patient. The polynucleotide is preferably a DNA sequence, such as a cDNA sequence, or a mRNA sequence that encodes for a protein that binds to a tumor epitope. With respect to the mRNA sequence, it is preferred that the mRNA sequences are selected based on the sequence of the tumor neoepitope, tumor associated antigen, or self-lipid that the T cell receptor protein complex targets to. The T cell receptors may be selected from those encoding sequences drawn from exhausted T cells of a patient. For example, it is preferred that the peptide encoded by the polynucleotide has an actual or predicted affinity to the tumor epitope at least with a KD of at least equal or less than $10^{-6}$M, preferably at least equal or less than $10^{-7}$M, more preferably at least equal or less than $10^{-8}$M. Any suitable methods to identify the polynucleotide sequence that has high binding affinity to the tumor epitope are contemplated. For example, a nucleic acid sequence of polynucleotide can be identified via a mass screening of peptides having various affinities to the tumor epitope via any suitable in vitro assays (e.g., flow cytometry, SPR assay, a kinetic exclusion assay, etc.), or by mRNA display technique (e.g., RNA bind-n-seq, etc.).

In still other contemplated embodiments, the polynucleotide includes a nucleic acid segment encoding a signaling peptide that directs the recombinant protein to the cell surface. Any suitable and/or known signaling peptides are contemplated (e.g., leucine rich motif, etc.).

In some embodiments, the polynucleotide also includes a sequence element that controls expression of the recombinant protein, and all manners of control are deemed suitable for use herein. For example, where the recombinant nucleic acid is an RNA, expression control may be exerted by suitable translation initiation sites (e.g., suitable cap structure, initiation factor binding sites, internal ribosome entry sites, etc.) and a polyA tail (e.g., where length controls stability and/or turnover), while recombinant DNA expression may be controlled via a constitutively active promoter, a tissue specific promoter, or an inducible promoter.

The recombinant nucleic acids can be reintroduced into immunocompetent cells such as T cells by any suitable means. Preferably, the recombinant nucleic acid can be inserted into a suitable vector to be introduced to and expressed in the T cells. The suitable vector includes, but not limited to, any mammalian cell expression vector and a viral vector, depending on the methodology of introducing the recombinant nucleic acid to the cells. Alternatively, where the recombinant nucleic acid(s) is/are RNA, the nucleic acid may be transfected into the cells. It should also be recognized that the manner of recombinant expression is not limited to a particular technology so long as the modified cells are capable of producing the chimeric protein in a constitutive or inducible manner. Therefore, the cells may be transfected with linear DNA, circular DNA, linear RNA, a DNA or RNA virus harboring a sequence element encoding the chimeric protein, etc. Viewed form a different perspective, transfection may be performed via ballistic methods, virus-mediated methods, electroporation, laser poration, lipofection, genome editing, liposome or polymer-mediated transfection, fusion with vesicles carrying recombinant nucleic acid, etc.

Thus, it should also be appreciated that the recombinant nucleic acid may be integrated into the genome (via genome editing or retroviral transfection) or may be present as a stable or transient extrachromosomal unit (which may have replicating capability). For example, the recombinant nucleic acid that is used to transfect the cytotoxic cell may be configured as a viral nucleic acid and suitable viruses to transfect the cells include adenoviruses, lentiviruses, adeno-associated viruses, parvoviruses, togaviruses, poxviruses, herpes viruses, etc. Alternatively, the recombinant nucleic acid may also be configured as extrachromosomal unit (e.g., as plasmid, yeast artificial chromosome, etc.), or as a construct suitable for genome editing (e.g., suitable for CRISPR/Cas9, Talen, zinc-finger nuclease mediated integration), or may be configured for simple transfection (e.g., as RNA, DNA (synthetic or produced in vitro), PNA, etc.). Therefore, it should also be noted that the cells may be transfected in vitro or in vivo.

The inventors also contemplate that ex vivo expanded and optionally activated genetically modified T cells can be administered to a patient having a tumor or cancer (or suffering from a viral infection such as a retroviral infection). It is contemplated that the T cells (e.g., isolated, isolated and ex vivo expanded, genetically modified, etc.) and/or genetically engineered T cells can be formulated in any pharmaceutically acceptable carrier (e.g., as a sterile injectable composition) with a cell titer of at least $1 \times 10^3$ cells/ml, preferably at least $1 \times 10^5$ cells/ml, more preferably at least $1 \times 10^6$ cells/ml, and at least 1 ml, preferably at least 5 ml, more preferably and at least 20 ml per dosage unit. However, alternative formulations are also deemed suitable for use herein, and all known routes and modes of administration are contemplated herein. As used herein, the term "administering" T cells and/or genetically modified T cells refers to both direct and indirect administration of the T cells and/or genetically modified T cells formulation, wherein direct administration of T cells and/or genetically modified T cells is typically performed by a health care professional (e.g., physician, nurse, etc.), and wherein indirect administration includes a step of providing or making available the T cells and/or genetically modified T cell formulation to the health care professional for direct administration (e.g., via injection, etc.).

While the composition can comprise only genetically modified T cells, it is also contemplated that the composition can comprise a mixture of expanded T cells and genetically modified T cells. In this composition, the ratio of expanded T cells and genetically modified T cells may vary based on the type of cancer, age, gender, or health status of the patient, size of tumor, or T cell counts in the patient's blood. In some embodiments, the ratio of genetically modified T cells and expanded T cells is at least 1:1, at least 2:1, at least 3:1, at least 5:1, or at least 1:2, at least 1:3, or at least 1:5.

In some embodiments, the expanded T cells and/or genetically modified T cell formulation is administered via systemic injection including subcutaneous, subdermal injection, or intravenous injection. In other embodiments, where the systemic injection may not be efficient (e.g., for brain tumors, etc.), it is contemplated that the T cells and/or genetically modified T cell formulation is administered via intratumoral injection.

With respect to dose of the T cell formulation administration, it is contemplated that the dose may vary depending on the status of disease, symptoms, tumor type, size, location, patient's health status (e.g., including age, gender, etc.), and any other relevant conditions. While it may vary, the dose and schedule may be selected and regulated so that the T cells and/or genetically modified T cells do not provide any significant toxic effect to the host normal cells, yet sufficient to be effective to induce an cytotoxic effect and/or immune-modulatory effect against the tumor and/or the tumor microenvironment such that size of the tumor is decreased (e.g., at least 5%, at least 10%, at least 20%, etc.), the number of tumor cells is decreased, the phenotype of the tumor may be changed (e.g., shape, change in gene expression, change in protein expression, change in post-translational modification of a protein, etc.), the accumulation of MDSC and/or Tregs may be prevented (or stopped, decreased, etc.).

With respect to the schedule of administration, it is contemplated that it may also vary depending on the status of disease, symptoms, tumor type, size, location, patient's health status (e.g., including age, gender, etc.), and any other relevant conditions. In some embodiments, a single dose of T cells and/or genetically modified T cell formulation can be administered at least once a day or twice a day (half dose per administration) for at least a day, at least 3 days, at least a week, at least 2 weeks, at least a month, or any other desired schedule. In other embodiments, the dose of the T cells and/or genetically modified T cell formulation can be gradually increased during the schedule, or gradually decreased during the schedule. In still other embodiments, several series of administration of T cells and/or genetically modified T cell formulation can be separated by an interval (e.g., one administration each for 3 consecutive days and one administration each for another 3 consecutive days with an interval of 7 days, etc.).

In some embodiments, the dose and schedule of the T cell formulation administration may be fine-tuned and informed by cellular changes of the infected cells or cancer cells. For example, after a cancer patient is administered with one or more dose of the T cell formulation, a small biopsy of the cancer tissue may be obtained in order to assess any changes (e.g., upregulation of NKG2D ligand, apoptosis rate, etc.) resulted from interaction with the genetically modified NK cell formulation. The assessment of cellular changes can be performed by any suitable types of technology, including immunohistochemical methods (e.g., fluorescence labeling, in-situ hybridization, etc.), biochemical methods (e.g., quantification of proteins, identification of post-translational modification, etc.), or omics analysis. Based on the result of the assessment, the dose and/or schedule of the genetically modified T cell formulations can be modified (e.g., lower dose if excessive cytotoxicity is observed, etc.).

Genetically modified T cells are activated upon recognition of MHC class I-antigen complex on the antigen presenting cells to elicit immune response against the antigen presenting cells by releasing multiple cytokines and chemokines (such as IL-2, Interleukin-13, Interleukin-17, Interleukin-21, and TNF-alpha). Thus, in addition to administering T cells to the patient, preferably to the tumor or tumor microenvironment, pre-conditioning of the tumor to promote a condition in which the tumor is more susceptible to administered T cells is especially contemplated.

For example, in some embodiments, the tumor cells can be preconditioned to genetically modified T cell-susceptible (or responsive) conditions and followed by in vivo expansion of genetically modified T cells. In such embodiments, the genetically modified T cells can be expanded by applying (preferably locally applying near the tumor) activating molecules, including but not limited to, cytokines (e.g., IL-2, IL-5, IL-7, IL-8, IL-12, IL-12, IL-15, IL-18, and IL-21, preferably human recombinant IL-2, IL-5, IL-7, IL-8, IL-12, IL-12, IL-15, IL-18, and IL-21, etc.) in any desirable concentration (e.g., at least 10 U/ml, at least 50 U/ml, at least 100 U/ml), T cell receptor antibodies (e.g., anti-CD2, anti-CD3, anti-CD28, α-TCR-Vα24+ antibodies, preferably immobilized on beads, etc.), a glycolipid (e.g., α-GlcCer, etc.), a glycolipid coupled with CD1 (e.g., CD1d, etc.). The amount of in vivo expanded genetically modified T cells can be determined by counting the genetically modified NK cells from a biopsy tissue or from a locally collected bodily fluid.

While any suitable conditions that can increase the susceptibility or responsiveness of the cancer cells to the genetically modified T cells are contemplated, it is most preferred that the tumor cells are treated with a condition to express a universally recognized antigen such as a CD1 or CD1 coupled with a peptide or lipid antigen on the cell surface. In some embodiments, a recombinant nucleic acid encoding the universally recognized antigen (wild-type or modified) can be introduced to the cancer cells so that the universally recognized antigen molecule is overexpressed in the tumor. Preferably, the recombinant nucleic acid encoding the universally recognized antigen is inserted into a viral genome and introduced to the cancer cells. Any suitable virus to carry recombinant nucleic acid encoding the universally recognized antigen is contemplated. The suitable virus include oncolytic virus, preferably genetically modified oncolytic virus presenting low immunogenicity to the host. For example, a preferred oncolytic virus includes genetically modified adenovirus serotype 5 (Ad5) with one or more deletions in its early 1 (E1), early 2b (E2b), or early 3 (E3) gene (e.g., E1 and E3 gene-deleted Ad5 (Ad5[E1]), E2b gene-deleted Ad5 (Ad5[E1,E2b], etc.). In one preferred virus strains having Ad5 [E1–, E2b–] vector platform, early 1 (E1), early 2b (E2b), and early 3 (E3) gene regions encoding viral proteins against which cell mediated immunity arises, are deleted to reduce immunogenicity. Also, in this strain, deletion of the Ad5 polymerase (pol) and preterminal protein (pTP) within the E2b region reduces Ad5 downstream gene expression which includes Ad5 late genes that encode highly immunogenic and potentially toxic proteins. Viewed from a different perspective and among other suitable viruses, particularly preferred oncolytic viruses include non-replicating or replication deficient adenoviruses.

Preferably, a recombinant nucleic acid encoding a universally recognized antigen such as CD1 includes a nucleic acid segment encoding a signaling peptide that directs the universally recognized antigen to the cell surface. Any suitable and/or known signaling peptides are contemplated (e.g., leucine rich motif, etc.). Preferably, the nucleic acid segment encoding the universally recognized antigen is located in the upstream of the nucleic acid segment encoding signaling peptide such that the signal sequence can be located in C-terminus of the antigen. However, it is also contemplated that the signaling peptide can be located in the N-terminus of or in the middle of the universally recognized antigen such as CD1.

Additionally, the recombinant nucleic acid encoding a universally recognized antigen such as CD1 may include a nucleic acid segment encoding a peptide ligand of universally recognized antigen such as CD1 (e.g., a hydrophobic short peptide), for example, p99. In this embodiment, the recombinant nucleic acid may include a first nucleic acid segment encoding universally recognized antigen such as CD1 and a second nucleic acid segment encoding p99, and the first and second nucleic acid segments are separated by a nucleic acid sequences encoding a type of 2A self-cleaving peptide (2A) so that the universally recognized antigen such as CD1 and p99 can be translated into two separate and distinct peptide, yet the expression of two peptides can be regulated under the same promoter. The inventors contemplate that the co-expressed universally recognized antigen such as CD1 and p99 are coupled intracellularly, trafficked together to the tumor cell surface, and trigger genetically modified T cell activation when the genetically modified NK cell recognizes the tumor cells via universally recognized antigen such as CD1 receptor interaction or MHC-epitope-T cell receptor (or CAR) interaction. It should be noted that in at least some instances, p99 may be bound to universally recognized antigen such as CD1 in an unorthodox manner that may disrupt conventional T cell recognition. However, as p99 appears to be a strong ligand with physiological signaling capability, other interactions (with T cells or other immune competent cells) are also contemplated herein.

In other embodiments, the tumor cells can be subjected to conditions or pretreated with any composition that can stress the tumor cells to increase expression of a tumor associated antigen. For example, local heat shock treatment (e.g., at 42 degree Celsius for 1 min, for 3 min, for 5 min, etc.), hypoxia, chemotherapy, exposure to toxins, low dose radiation, and/or mechanical damage (e.g., partial surgical removal of cancer tissue, etc.).

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise. Where the specification claims refers to at least one of something selected from the group consisting of A, B, C . . . and N, the text should be interpreted as requiring only one element from the group, not A plus N, or B plus N, etc.

What is claimed is:

1. A method of in-vitro primary T cell growth, comprising:
    enriching T cells in a blood sample;
    stimulating the T cells with an anti-CD2 antibody, an anti-CD3 antibody, and/or an anti-CD28 antibody;
    expanding the T cells in the presence of IL-2, IL-7, and IL-15 to at least 30-fold expansion,
        wherein the step of expansion comprises serial dilution of the T cells by increasing the culture volume by at least 2-fold at least once every 7 days,
        wherein the serial dilution is carried out in a single and continuous culture device having an inlet and exit of cell culture medium to permit adequate flow to growth surfaces;
    harvesting the expanded T cells; and
    cryopreserving the expanded T cells at a concentration of 10 million to 15 million cells per milliliter.

2. The method of claim 1, wherein the blood sample is enriched in peripheral blood mononuclear cells (PMBC).

3. The method of claim 1, wherein the step of expanding the T cells with the at least one cytokine comprises serial dilution of the T cells and the cytokine in cell culture medium.

4. The method of claim 3, wherein the cell culture medium is optimized to culture human T-cells.

5. The method of claim 3, wherein the cell culture medium further comprises human serum.

6. The method of claim 5, wherein the human serum is at least 10% of the total volume of the cell culture medium.

7. The method of claim 1 wherein the method is performed in a Good Manufacturing Practice (GMP) in-a-box system.

8. The method of claim 1, wherein the method further comprises phenotyping the expanded T cells.

9. The method of claim 1, wherein the method further comprises transfecting the expanded T cells.

* * * * *